(12) United States Patent
Masuda

(10) Patent No.: US 11,512,061 B2
(45) Date of Patent: Nov. 29, 2022

(54) AMMONIUM SALT HAVING SACCHARIN ANION

(71) Applicant: Nisshinbo Holdings Inc., Tokyo (JP)

(72) Inventor: Gen Masuda, Chiba (JP)

(73) Assignee: NISSHINBO HOLDINGS INC., Tokyo (JP)

( * ) Notice: Subject to any disclaimer, the term of this patent is extended or adjusted under 35 U.S.C. 154(b) by 0 days.

(21) Appl. No.: 17/299,486

(22) PCT Filed: Oct. 29, 2019

(86) PCT No.: PCT/JP2019/042262
§ 371 (c)(1),
(2) Date: Jun. 3, 2021

(87) PCT Pub. No.: WO2020/121667
PCT Pub. Date: Jun. 18, 2020

(65) Prior Publication Data
US 2022/0064131 A1    Mar. 3, 2022

(30) Foreign Application Priority Data

Dec. 14, 2018 (JP) ............................ JP2018-233958

(51) Int. Cl.
| | |
|---|---|
| C07D 275/06 | (2006.01) |
| C07C 211/63 | (2006.01) |
| C07D 295/08 | (2006.01) |
| C07D 295/088 | (2006.01) |

(52) U.S. Cl.
CPC .......... *C07D 275/06* (2013.01); *C07C 211/63* (2013.01); *C07D 295/088* (2013.01)

(58) Field of Classification Search
CPC .. C07D 295/088; C07D 275/06; C07C 211/63
See application file for complete search history.

(56) References Cited

U.S. PATENT DOCUMENTS

| | | |
|---|---|---|
| 2009/0236227 A1 | 9/2009 | Kuzmanovic et al. |
| 2016/0319449 A1 | 11/2016 | Izagirre Etxeberria et al. |

FOREIGN PATENT DOCUMENTS

| | | |
|---|---|---|
| CN | 1743320 A | 3/2006 |
| EP | 3 088 571 A1 | 11/2016 |
| JP | 2005-82534 A | 3/2005 |
| JP | 2005-232019 A | 9/2005 |
| JP | 2009-526910 A | 7/2009 |
| PL | 227121 B1 | 10/2017 |
| PL | 228317 B1 | 3/2018 |

OTHER PUBLICATIONS

KR 2014018461 (Choi, et al.) Feb. 13, 2014 (abstract) STN [database online]. Dongwoo Fine-Chem. Co., Ltd. [retrieved on Apr. 29, 2022], Accession No. 2014:261366.*
CN 102113484 (Chen, et al.) Jul. 6, 2011 (abstract) STN [database online]. Faming Zhuanli Shenqing [retrieved on Apr. 29, 2022], Accession No. 2011:856236.*
Frade, et al. (abstract) Green Chemistry (2009), 11 (10), 1660-1665 STN [database online] retrieved on Apr. 29, 2022], Accession No. 2009:1223115.*
WO 2005072376 (Davis, et al.) Aug. 11, 2005 (abstract) STN [database online]. PCT Int. Appl. [retrieved on Apr. 29, 2022] Accession No. 2005:729503.*
Niemczak et al., "Synthesis and properties of quaternary ammonium salts with trimethylvinylammanium cation", Przemysl Chemiczny, 2013, vol. 92, No. 9, pp. 1646-1648, cited in ISR (5 pages).
Diabate et al., "Syntheses and characterization of the analogues of glycine-betaine based ionic liquids with saccharinate anion: Application in the extraction of cadmium ion from aqueous solution", Journal of Molecular Liquids, Oct. 3, 2018, vol. 272, pp. 708-714, cited in ISR (7 pages).
International Search Report dated Dec. 3, 2019, issued in counterpart International Application No. PCT/JP2019/042262 (2 pages).

\* cited by examiner

*Primary Examiner* — Shawquia Jackson
(74) *Attorney, Agent, or Firm* — WHDA, LLP

(57) ABSTRACT

An ammonium salt having a saccharin anion, which is represented by formula (1), exhibits excellent thermal stability even though no halogen atom is contained therein.

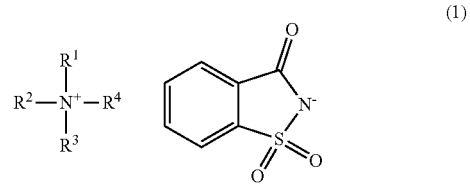

(In the formula, each of $R^1$-$R^4$ independently represents an alkyl group having 1-4 carbon atoms or an alkoxyalkyl group that is represented by —$(CH_2)_n$—OR (wherein R represents an alkyl group having 1-4 carbon atoms, and n represents an integer of 1 or 2). Incidentally, any two of the $R^1$-$R^4$ may combine with each other to form a ring together with a nitrogen atom.

5 Claims, 6 Drawing Sheets

AMMONIUM SALT HAVING SACCHARIN ANION

TECHNICAL FIELD

The invention relates to an ammonium salt having a saccharin anion.

BACKGROUND ART

Most of the conventionally known ionic liquids contain an anion including a halogen atom such as a fluorine atom, leading to a problem in terms of environmental load.

In addition, the high manufacturing cost is also a problem, and improvement of these problems has been awaited.

In particular, in the case of using an ionic liquid containing a halogen atom as a reaction solvent, there is concern about environmental problems during leakage and disposal of the ionic liquid.

In view of this point, ionic liquids free of a halogen atom have also been developed (see, for example, Patent Documents 1 and 2), but there are problems that, for example, such ionic liquids have higher viscosity and lower heat resistance (a lower decomposition point) than ionic liquids containing a halogen atom such as a fluorine atom.

PRIOR ART DOCUMENTS

Patent Documents

Patent Document 1: JP-A 2005-82534
Patent Document 2: JP-A 2005-232019

SUMMARY OF INVENTION

Technical Problem

The invention has been made in view of such a situation, and an object of the invention is to provide an ammonium salt free of a halogen atom and excellent in thermal stability.

Solution to Problem

As a result of intensive studies to attain the above object, the inventor has found that a predetermined quaternary ammonium salt having a saccharin anion has good thermal stability despite being free of a halogen, and that the ammonium salt is a liquid (ionic liquid) at 25° C. according to its cation structure, and completed the invention.

Accordingly, the invention provides an ammonium salt as defined below.

1. An ammonium salt having a saccharin anion, represented by the formula (1):

[Chem. 1]

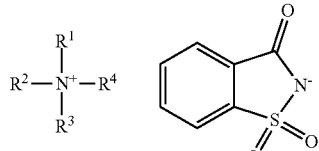

wherein $R^1$ to $R^4$ are each independently an alkyl group having 1 to 4 carbon atoms or an alkoxyalkyl group of —$(CH_2)_n$—OR wherein R is an alkyl group having 1 to 4 carbon atoms and n is an integer of 1 or 2, provided that any two of the $R^1$ to $R^4$ may combine with each other to form a ring together with a nitrogen atom.

2. The ammonium salt of the item 1, being an ionic liquid having a melting point of 25° C. or less.

3. The ammonium salt of the item 1 or 2 wherein any one of the $R^1$ to $R^4$ is the alkoxyalkyl group of —$(CH_2)_n$—OR, remaining three of the $R^1$ to $R^4$ are each independently an alkyl group having 1 to 4 carbon atoms, provided that any two of the remaining three of the $R^1$ to $R^4$ may combine with each other to form a ring together with the nitrogen atom.

4. The ammonium salt of any one of the items 1 to 3, having the formula (2):

[Chem. 2]

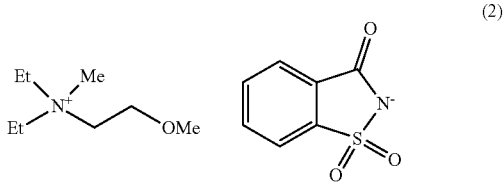

wherein Me is a methyl group, and Et is an ethyl group.

5. The ammonium salt of any one of the items 1 to 3, having the formula (3):

[Chem. 3]

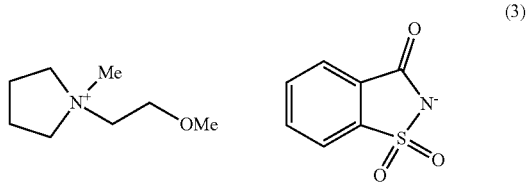

wherein Me is a methyl group.

6. The ammonium salt of any one of the items 1 to 3, having the formula (4):

[Chem. 4]

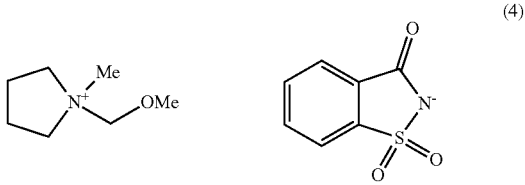

wherein Me is a methyl group.

Advantageous Effects of Invention

The ammonium salt of the invention is free of a halogen and has a saccharin anion as an anion, and therefore, has small environmental load. Meanwhile, despite being free of a halogen, the ammonium salt exhibits good heat resistance.

Furthermore, the ammonium salt is a liquid (ionic liquid) at 25° C. according to its cation structure, and the ionic liquid is excellent in safety and can be suitably used as an environmentally friendly reaction solvent.

DESCRIPTION OF EMBODIMENTS

Figure 1:
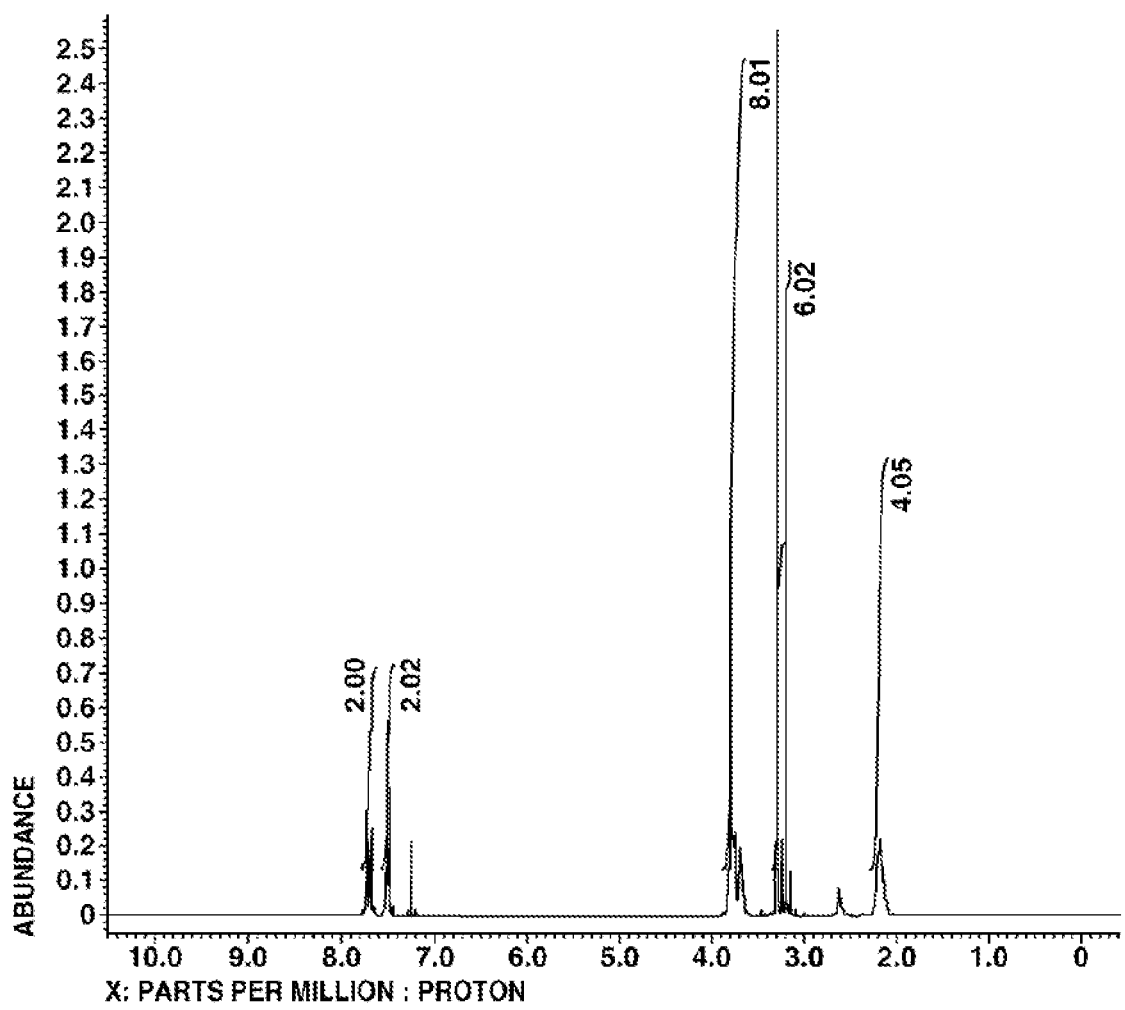
FIG. 1 is a $^1$H-NMR spectrum of a compound [1] obtained in Example 1.

Hereinafter, the invention is described in more detail.
The ammonium salt having a saccharin anion of the invention is represented by the formula (1).

[Chem. 5]

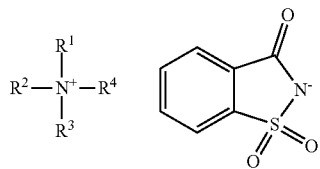

(1)

In the formula (1), $R^1$ to $R^4$ are each independently an alkyl group having 1 to 4 carbon atoms or an alkoxyalkyl group of —$(CH_2)_n$—OR wherein R is an alkyl group having 1 to 4 carbon atoms and n is an integer of 1 or 2, provided that any two of the $R^1$ to $R^4$ may combine with each other to form a ring together with a nitrogen atom.

The $R^1$ to $R^4$ and R may be a linear, branched, or cyclic alkyl group having 1 to 4 carbon atoms, and specific examples of the alkyl group include methyl, ethyl, n-propyl, i-propyl, c-propyl, n-butyl, i-butyl, s-butyl, t-butyl, and c-butyl groups. Among the groups, the alkyl groups having 1 to 3 carbon atoms are preferable, and the methyl and ethyl groups are more preferable.

Examples of the ring structure in which any two of the $R^1$ to $R^4$ combine with each other to form the ring together with the nitrogen atom include aziridine, azetidine, pyrrolidine, and piperidine rings, and among the rings, the pyrrolidine ring is preferable.

In particular, from the viewpoint that the ammonium salt is likely to be liquid as an ionic liquid at room temperature (25° C.), the ammonium salt of the invention preferably has, as any one of the $R^1$ to $R^4$, an alkoxyalkyl group of —$(CH_2)_n$—OR in which R is preferably an alkoxyalkyl group having 1 to 3 carbon atoms. The remaining three of the $R^1$ to $R^4$ preferably each independently have a cation structure that is alkyl group having 1 to 4, preferably 1 to 3 carbon atoms (provided that any two of the alkyl groups may combine with each other to form a ring together with the nitrogen atom), and more preferably each independently have any of the cation structures of the following formulae.

[Chem. 6]

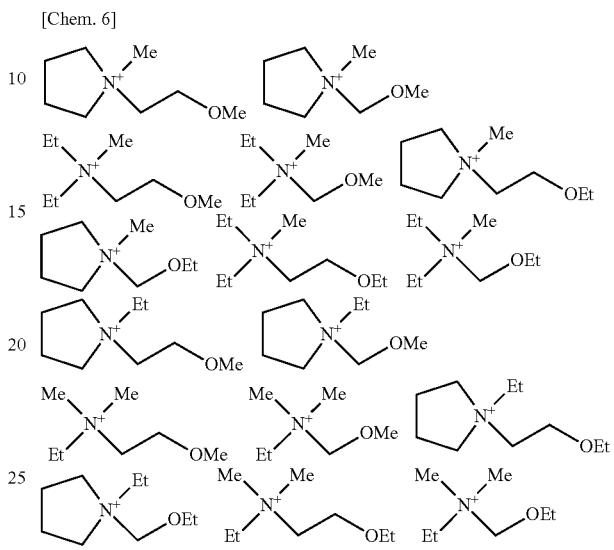

(In the formulae, Me is a methyl group, and Et is an ethyl group.)

The ammonium salt of the invention can be obtained through, for example, mixing a predetermined quaternary ammonium salt halide produced in accordance with a conventional method (such as a chloride or a bromide) and a commercially available saccharin metal salt (such as a sodium salt) in an organic solvent capable of dissolving the halide and the salt even partially (such as acetonitrile) for base exchange. In many cases, the saccharin salt produced as the desired product is dissolved in the solvent, and the inorganic salt as a by-product (such as a sodium chloride salt) is precipitated as a solid. Therefore, the desired product can be obtained through filtering the solution as it is and concentrating the solvent. If necessary, a high-purity product can be obtained through treating the predetermined quaternary ammonium salt halide with an OH-type strongly basic anion exchange resin for ion exchange of the halide ion with a hydroxide ion to obtain a quaternary ammonium salt hydroxide, and neutralizing the quaternary ammonium salt hydroxide with saccharin in an aqueous solvent.

After completion of the reaction, water is removed to obtain the desired product.

EXAMPLES

Examples are given below for further illustrating the invention although the invention is not limited thereto.
The analyzers and the conditions used in Examples are as follows.
[1] spectrum
Device: JNM-ECZ400S manufactured by JEOL Ltd.
Solvent: Deuterated chloroform
[2] DSC
Device: DSC 6200 manufactured by Seiko Instruments Inc.
Measurement condition:
Measurement was performed under the condition that the temperature was raised at a rate of 10° C. per minute from 25° C. to 40° C., lowered at a rate of 1° C. per minute from 40° C. to −70° C., held at −70° C. for 1 minute, and then raised at a rate of 1° C. per minute from −70° C. to 40° C.

[3] TG-DTA

Device: TG-DTA 6200 manufactured by Seiko Instruments Inc. ([Examples 2 and 3])

Thermo Plus TG8120 manufactured by Rigaku Corporation ([Example 1])

Measurement condition:

Measurement was performed under the condition that the temperature was raised at a rate of 10° C. per minute from 20° C. to 500° C. in an air atmosphere.

[Example 1] Synthesis of Compound [1]

[Chem. 7]

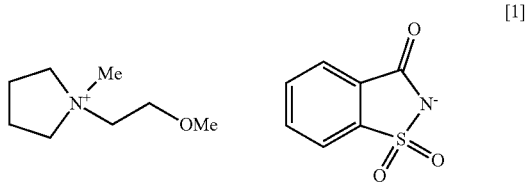

[1]

(In the formula, Me is a methyl group.)

Pyrrolidine (1.51 parts by weight) (manufactured by FUJIFILM Wako Pure Chemical Corporation) and 2-methoxyethyl chloride (1.00 part by weight) (manufactured by KANTO CHEMICAL CO., INC.) were mixed and reacted for 1 hour while refluxed. Through the reaction, the reaction solution was separated into two layers, and then allowed to cool for a while to solidify the lower layer. Only the upper layer was collected through decantation and purified through vacuum distillation to obtain 0.96 parts by weight of N-2-methoxyethylpyrrolidine (boiling point 76° C./vapor pressure 45 mmHg) as a desired product (yield 70%).

To 1.00 part by weight of the obtained N-2-methoxyethylpyrrolidine, tetrahydrofuran (THF) was added at 10 times the volume of the N-2-methoxyethylpyrrolidine, the resulting mixture was cooled in an ice bath, and 1.22 parts by weight of methyl iodide (manufactured by FUJIFILM Wako Pure Chemical Corporation) was added. After a while, a white solid was precipitated. After 30 minutes, the ice bath was removed, and the mixture was stirred at room temperature overnight. Then, the reaction solution was filtered wider reduced pressure to collect the precipitated white solid, and the white solid was recrystallized in an acetonitrile-tetrahydrofuran mixed solvent system to obtain 1.71 parts by weight of N-2-methoxyethyl-N-methylpyrrolidinium iodide (yield 81%).

To 1.00 part by weight of the obtained N-2-methoxyethyl-N-methylpyrrolidinium iodide, 2.00 parts by weight of ion-exchanged water was added, and the N-2-methoxyethyl-N-methylpyrrolidinium iodide was dissolved. Separately, a strongly basic ion exchange resin, ORLITE DS-2 (manufactured by ORGANO CORPORATION, exchange capacity 1.4 meq/ml, OH-type) was thoroughly washed so that the cleaning solution used for washing was neutral, and the ion exchange resin equivalent to 2.5 times the molar amount of the N-2-methoxyethyl-N-methylpyrrolidinium iodide was put into a plastic container and added to the N-2-methoxyethyl-N-methylpyrrolidinium iodide. After 6 to 7 hours, the ion exchange resin was filtered off with a Kiriyama funnel. To the filtrate, washed ORLITE DS-2 equivalent to 2.5 times the molar amount of the raw material was newly added and left overnight, and then the ion exchange resin was filtered off with a Kiriyama funnel to obtain a solution in which most of the salt was converted from the chloride salt to a hydroxide. Furthermore, the filtrate was flowed through a column packed with ORLITE DS-2 (equivalent to 5 times the molar amount of the raw material) at a space velocity SV=1 for treatment to obtain a hydroxide aqueous solution for a neutralization reaction.

Figure 2:
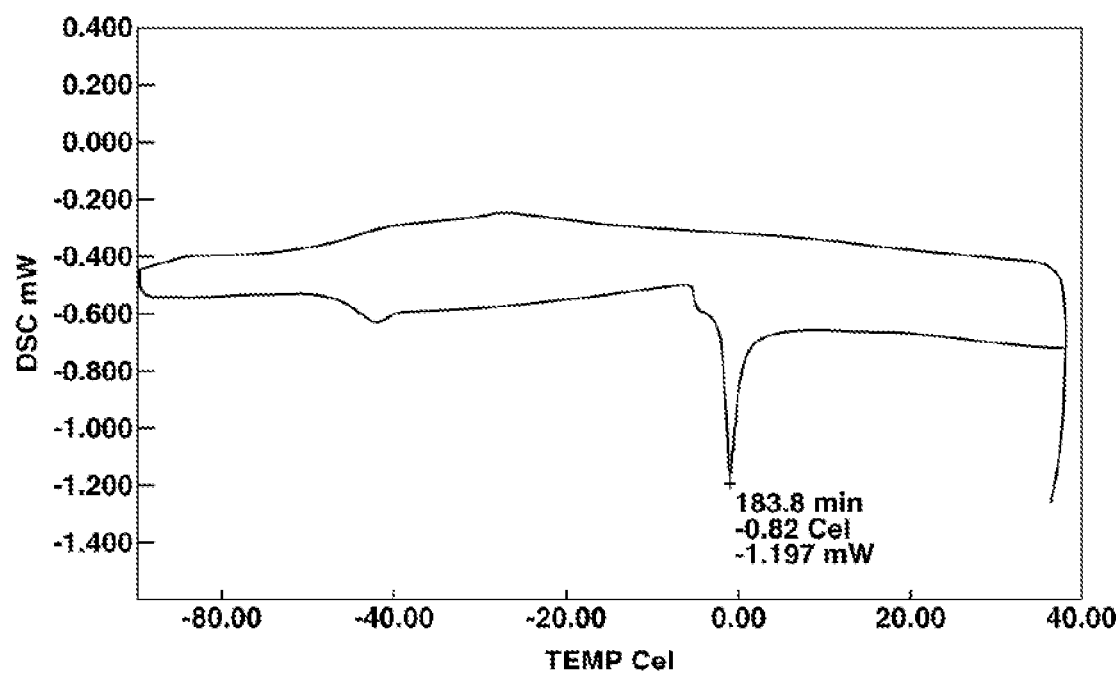
FIG. 2 is a differential scanning calorimetry (DSC) chart of the compound [1] obtained in Example 1.
Figure 3:
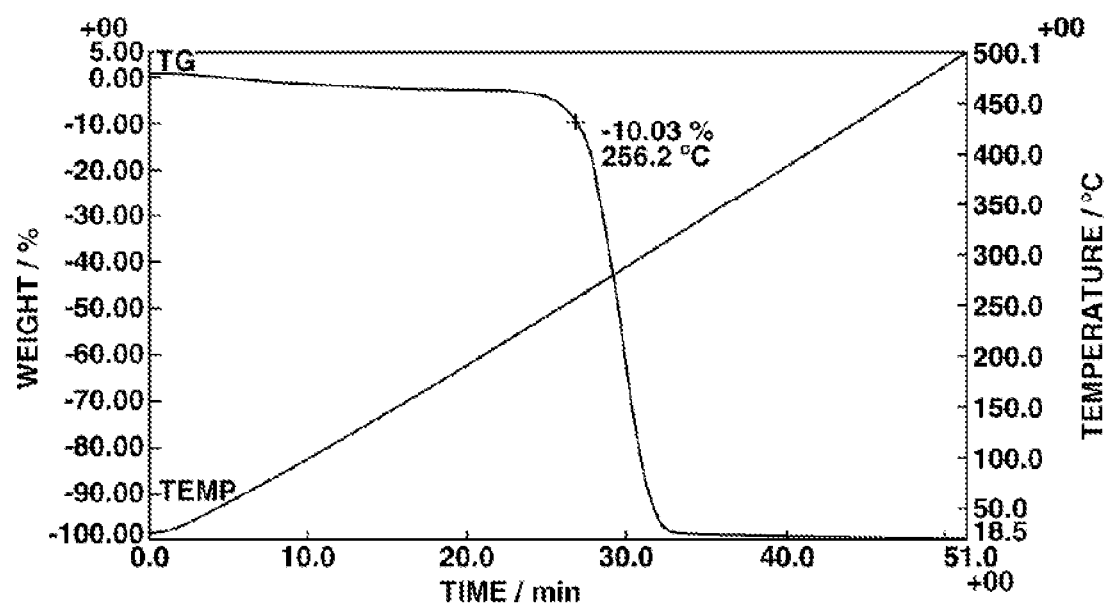
FIG. 3 is a thermogravimetry-differential thermal analysis (TG-DTA) chart of the compound [1] obtained in Example 1.

To the hydroxide aqueous solution, 0.61 parts by weight of saccharin (also known as o-sulfobenzimide, manufactured by Tokyo Chemical Industry Co., Ltd.) was added, and the resulting mixture was stirred to dissolve the saccharin. Then, saccharin was added little by little while the pH was checked with a pH test paper, and the mixing was completed when the pH test paper showed a pH of 7. From the aqueous solution, most of the water was removed with an evaporator, and then the resulting product was put under vacuum using a vacuum pump at 45° C. (using an oil bath) for 3 hours or more to obtain a desired product, 1.11 parts by weight of N-2-methoxyethyl-N-methylpyrrolidinium saccharinate (compound [1]) as a colorless transparent liquid (25° C.) (yield 92%). FIG. 1 shows the $^1$H-NMR chart (solvent: deuterated chloroform), FIG. 2 shows the DSC chart, and FIG. 3 shows the TG-DTA chart.

[Example 2] Synthesis of Compound [2]

[Chem. 8]

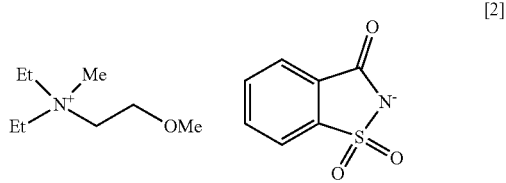

[2]

(In the formula, Me is a methyl group, and Et is an ethyl group.)

Diethylamine (1.00 part by weight) (manufactured by KANTO CHEMICAL CO., INC.) and 2-methoxyethyl chloride (1.24 parts by weight) (manufactured by KANTO CHEMICAL CO., INC.) were mixed, and the resulting mixed solution was put in an autoclave and reacted at 100° C. for 24 hours. At this time, the internal pressure was 1.3 kgf/cm$^2$. After 24 hours, to the mixture of a precipitated crystal and the reaction solution, an aqueous solution was added in which 0.79 parts by weight of potassium hydroxide (manufactured by KATAYAMA CHEMICAL INDUSTRIES Co., Ltd.) was dissolved in 2.00 parts by weight of water to obtain two organic layers, and the two organic layers were separated with a separatory funnel. Furthermore, an operation was performed twice in which 1.87 parts by weight of methylene chloride (manufactured by FUJIFILM Wako Pure Chemical Corporation) was added and extraction was performed. The separated organic layers were put together, washed with saturated brine, potassium carbonate (manufactured by FUJIFILM Wako Pure Chemical Corporation) was added, and the resulting mixture was dried and filtered under reduced pressure. The solvent of the obtained organic layer was removed using a rotary evaporator, the residue was distilled at atmospheric pressure, and a fraction having a boiling point of around 135° C. was obtained to obtain 0.26 parts by weight of N,N-diethyl-N-2-methoxyethylamine as a desired product (yield 30%).

Figure 4:
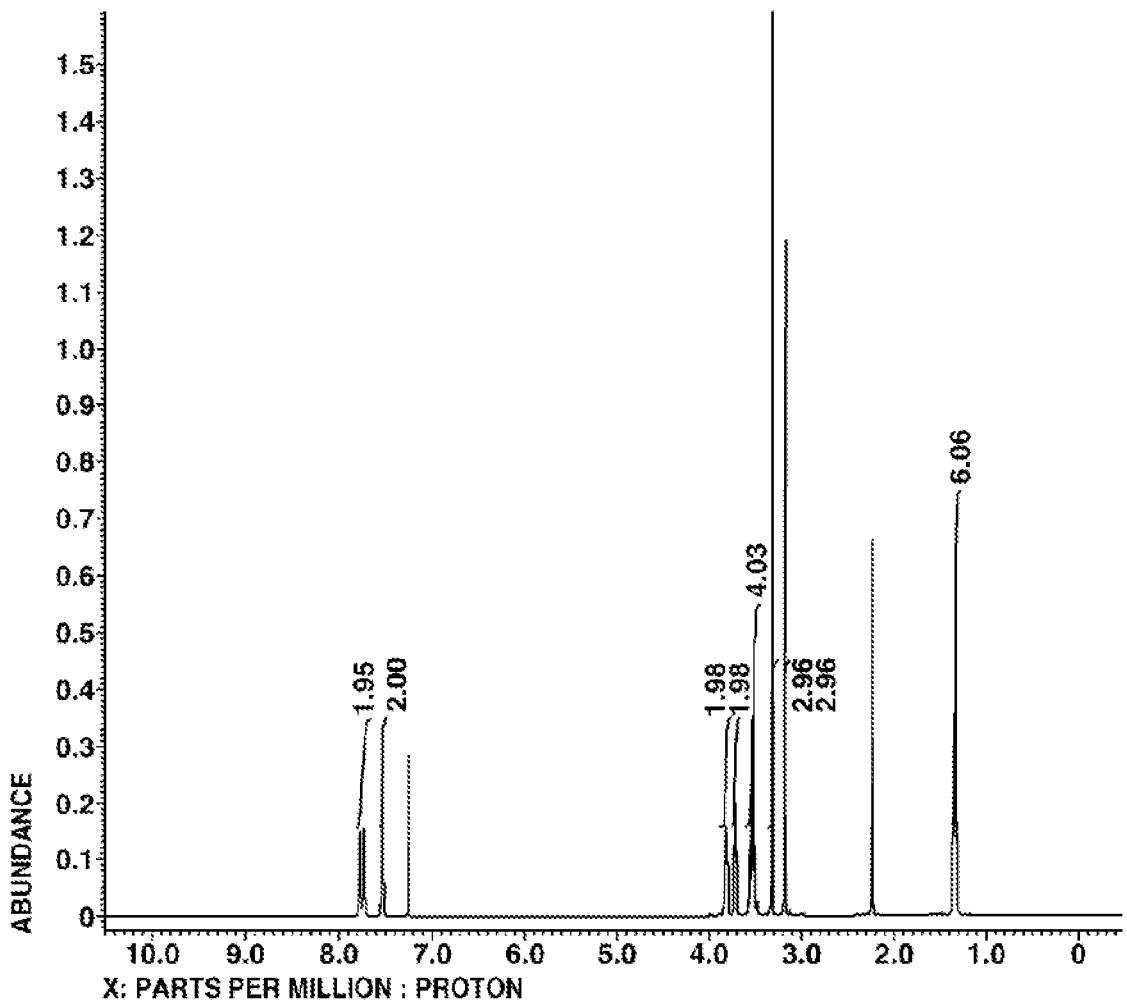
FIG. 4 is a $^1$H-NMR spectrum of a compound [2] obtained in Example 2.
Figure 5:
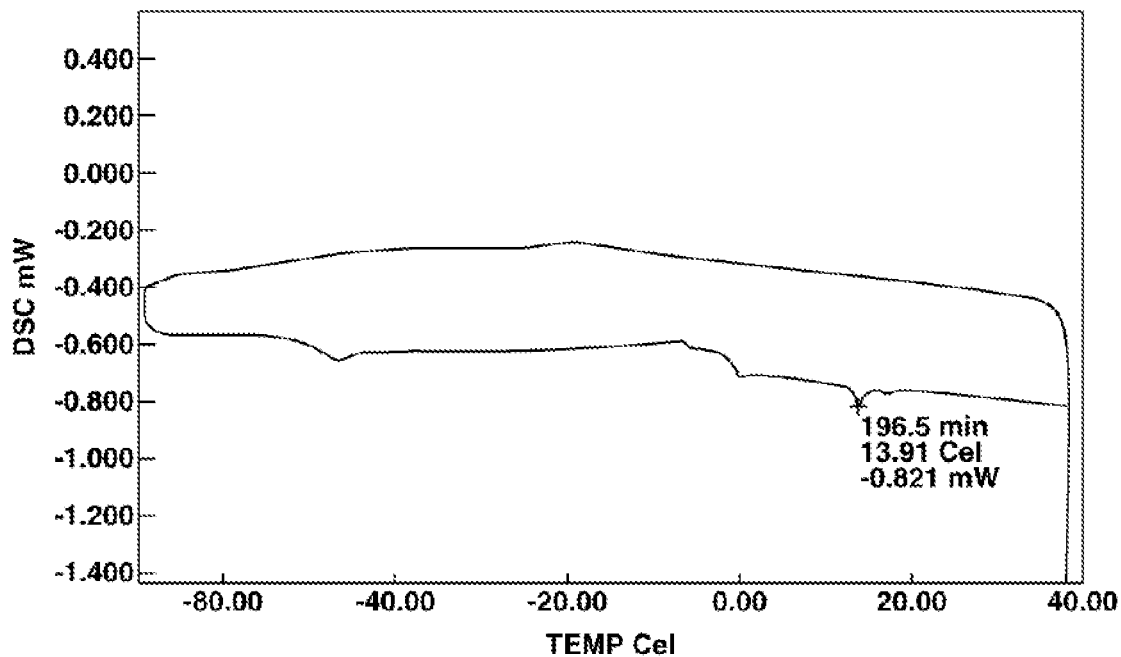
FIG. 5 is a DSC chart of the compound [2] obtained in Example 2.
Figure 6:
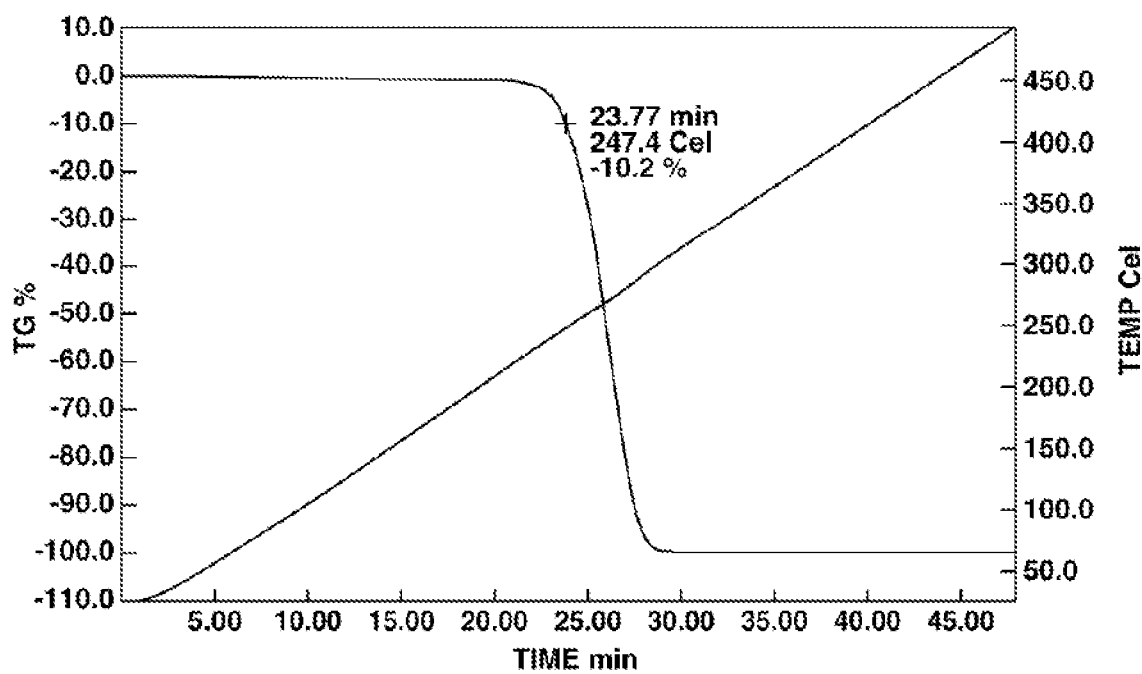
FIG. 6 is a TG-DTA chart of the compound [2] obtained in Example 2.

As a colorless transparent liquid (25° C.), 1.12 parts by weight of N,N-diethyl-N-methyl-N-(2-methoxyethyl)ammonium saccharinate (compound [2]) was obtained in the same manner as in Example 1 except that the N,N-diethyl-N-2-methoxyethylamine obtained above was used in place of N-2-methoxyethylpyrrolidine (yield 93%). FIG. 4 shows the $^1$H-NMR chart (solvent: deuterated chloroform), FIG. 5 shows the DSC chart, and FIG. 6 shows the TG-DTA chart.

[Example 3] Synthesis of Compound [3]

[Chem. 9]

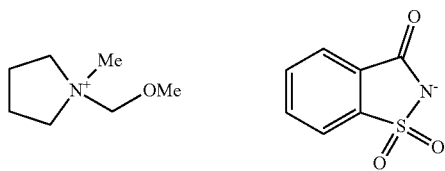

[3]

(In the formula, Me is a methyl group.)

To 22.2 parts by weight of 1-methylpyrrolidine (manufactured by FUJIFILM Wako Pure Chemical Corporation), tetrahydrofuran (THF) was added at 10 times the volume of the 1-methylpyrrolidine, and while the resulting mixture was cooled with ice and stirred, 21.1 parts by weight of chloromethyl methyl ether (manufactured by Tokyo Chemical Industry Co., Ltd.) was added. Although a crystal was immediately precipitated, the mixture was kept to be stirred overnight. Then, the reaction solution was filtered under reduced pressure to collect the precipitated solid, the solid was dried under reduced pressure using a vacuum pump to obtain 38.2 parts by weight of N-methoxymethyl-N-methylpyrrolidinium chloride as a white solid (yield 89%).

To 15.7 parts by weight of saccharin sodium dihydrate (manufactured by Tokyo Chemical Industry Co., Ltd.), methanol was added at 10 times the volume of the saccharin sodium dihydrate, and the resulting mixture was stirred to dissolve the saccharin sodium dihydrate. To the resulting solution, a solution was added in which 10.8 parts by weight of the N-methoxymethyl-N-methylpyrrolidinium chloride synthesized above was dissolved in methanol having a volume of 15 times of the N-methoxymethyl-N-methylpyrrolidinium chloride, and the resulting mixture was reacted overnight at room temperature.

Figure 7:
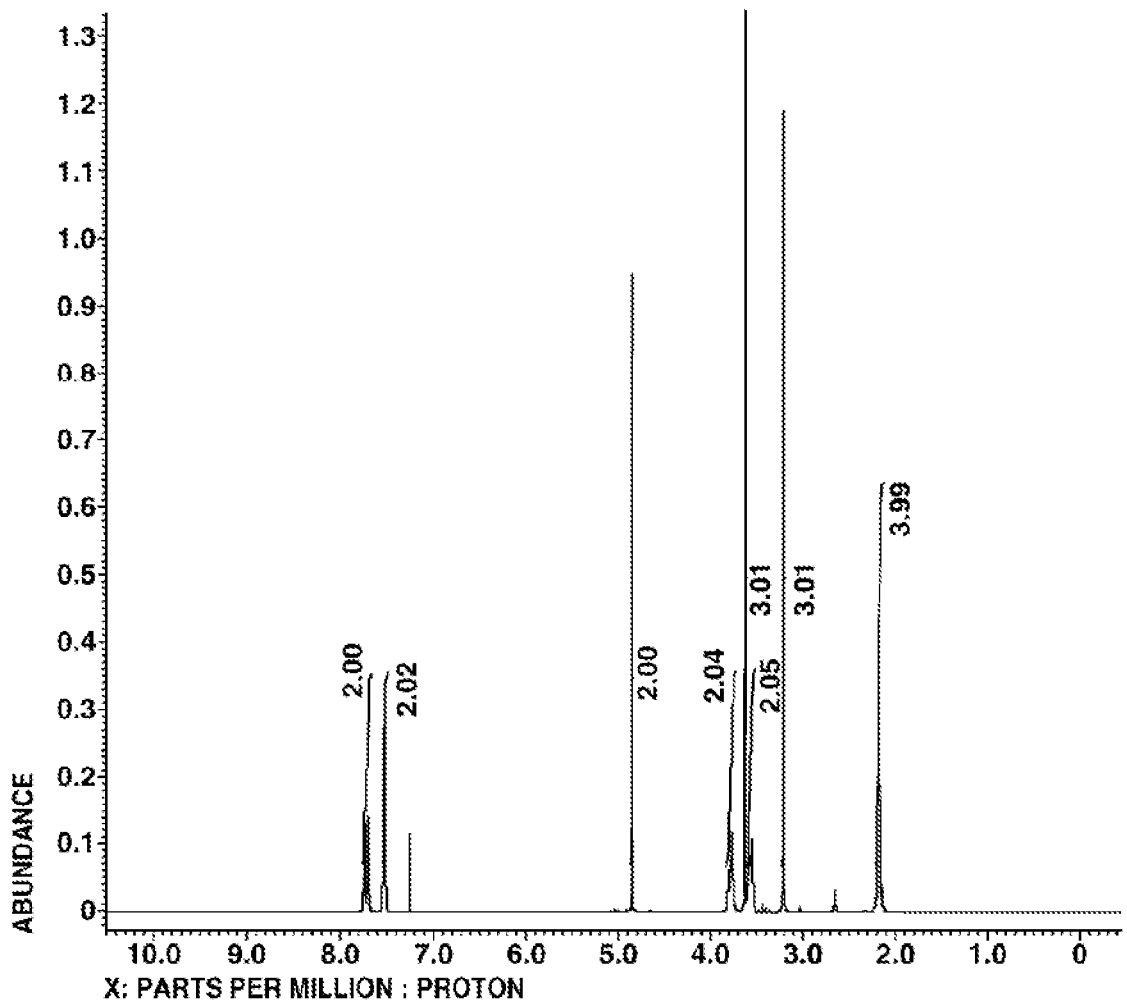
FIG. 7 is a $^1$H-NMR spectrum of a compound [3] obtained in Example 3.
Figure 8:
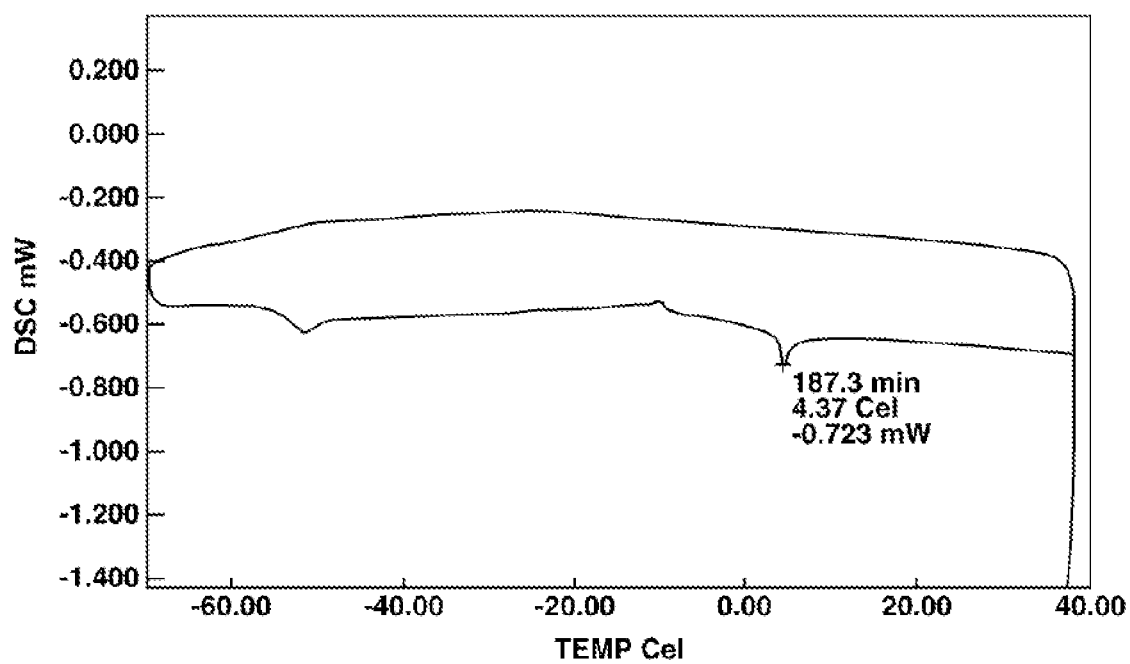
FIG. 8 is a DSC chart of the compound [3] obtained in Example 3.
Figure 9:
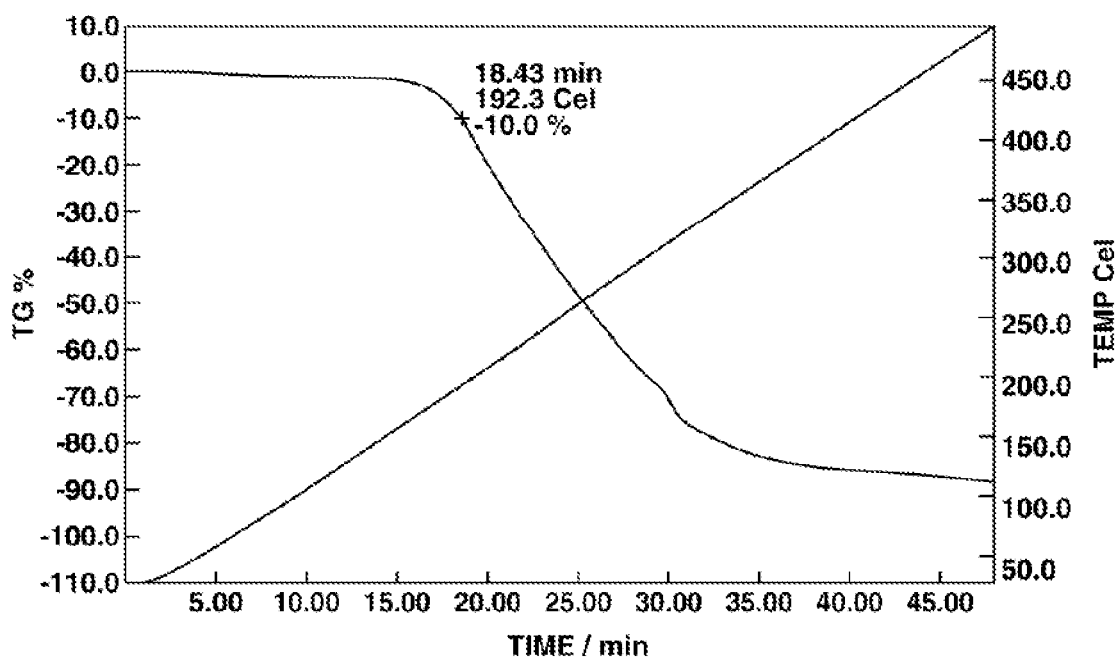
FIG. 9 is a TG-DTA chart of the compound [3] obtained in Example 3.

The reaction solution was concentrated, put under vacuum, and then dissolved in a minimized amount of acetonitrile. The resulting solution was added to a large amount of toluene, and a precipitated solid was filtered off. The filtrate was concentrated, the above-described operation was performed once again, and then the filtrate was concentrated and dried under reduced pressure using a vacuum pump to obtain a desired product, 18.9 parts by weight of N-methoxymethyl-N-methylpyrrolidinium saccharinate (compound [3]) as a colorless transparent liquid (25° C.) (yield 93%). FIG. 7 shows the $^1$H-NMR chart (solvent: deuterated chloroform), FIG. 8 shows the DSC chart, and FIG. 9 shows the TG-DTA chart.

The invention claimed is:
1. An ammonium salt having a saccharin anion, represented by formula (1):

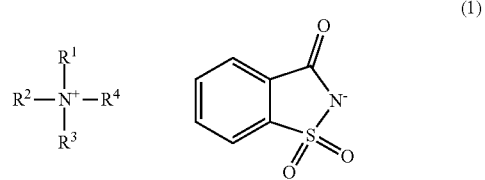

(1)

wherein any one of the $R^1$ to $R^4$ is an alkoxyalkyl group of —$(CH_2)_n$—OR wherein R is an alkyl group having 1 to 4 carbon atoms and n is an integer of 1 or 2, remaining three of the $R^1$ to $R^4$ are each independently an alkyl group having 1 to 4 carbon atoms, provided that any two of the remaining three of the $R^1$ to $R^4$ may combine with each other to form a ring together with the nitrogen atom.

2. The ammonium salt of claim 1, being an ionic liquid having a melting point of 25° C. or less.

3. The ammonium salt of claim 1, having the formula (2):

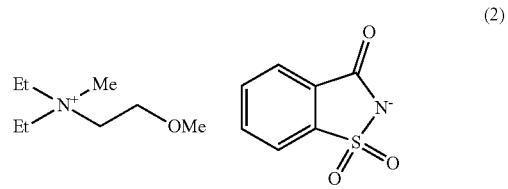

(2)

wherein Me is a methyl group, and Et is an ethyl group.

4. The ammonium salt of claim 1, having the formula (3):

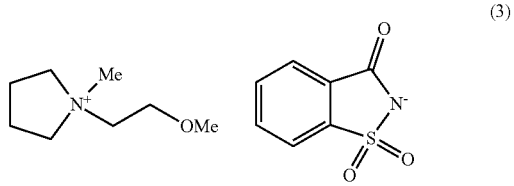

(3)

wherein Me is a methyl group.

5. The ammonium salt of claim 1, having the formula (4):

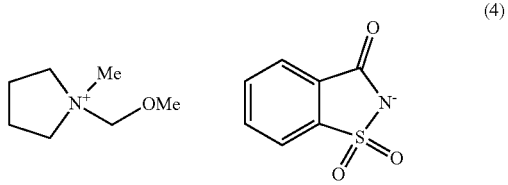

(4)

wherein Me is a methyl group.

* * * * *